(12) United States Patent
Hachisuka (10) Patent No.: US 7,532,316 B2
(45) Date of Patent: May 12, 2009

(54) DISPLAY PANEL INSPECTION APPARATUS AND METHOD

(75) Inventor: Seiji Hachisuka, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 102 days.

(21) Appl. No.: 11/710,507

(22) Filed: Feb. 26, 2007

(65) Prior Publication Data
US 2008/0030725 A1 Feb. 7, 2008

(30) Foreign Application Priority Data
Aug. 2, 2006 (JP) ............................... 2006-210847

(51) Int. Cl.
G01N 21/00 (2006.01)
(52) U.S. Cl. .................. 356/237.1; 356/239.1; 349/192
(58) Field of Classification Search ... 356/237.1–237.5, 356/239.1–239.2; 345/87; 349/55, 192; 714/E11.163; 250/208.1
See application file for complete search history.

(56) References Cited

U.S. PATENT DOCUMENTS 5,764,209 A * 6/1998 Hawthorne et al. ........... 345/87

2005/0280822 A1* 12/2005 Zeng .......................... 356/402

FOREIGN PATENT DOCUMENTS

| JP | 08128920 | * | 5/1996 |
| JP | 08178795 A | * | 7/1996 |
| JP | 11-119684 A | | 4/1999 |

* cited by examiner

Primary Examiner—Hoa Q Pham
(74) Attorney, Agent, or Firm—Westerman, Hattori, Daniels & Adrian, LLP.

(57) ABSTRACT

The present invention relates to a display panel inspection apparatus for inspecting a display panel composed of a plurality of pixels. The display panel inspection apparatus comprises a detecting unit detecting whether or not each of the pixels is a defective pixel and a holding unit holding a result of the detection by the detecting unit, thereby enabling reliable and easy detection of a defective pixel occurring temporarily due to variations of operation environment such as semi-contact trouble or semi-disconnection trouble, and others.

17 Claims, 8 Drawing Sheets

DISPLAY PANEL INSPECTION APPARATUS AND METHOD

BACKGROUND OF THE INVENTION

1) Field of the Invention

The present invention relates to a display panel inspection apparatus and method suitable for use in detection of line omission troubles in a display panel such as LCD (Liquid Crystal Display).

2) Description of the Related Art

In general, it is known that a display panel such as LCD (Liquid Crystal Display) sometimes contains defective pixels which do not fulfill their intended function.

In addition, dot omission troubles due to the appearance of defective pixels in units of pixel and line omission troubles due to the continuous appearance of defective pixels in the form of a line are commonly known as such defective pixels of a display panel.

If a display panel contains defective pixels, the defective pixels cause defects such as difficulty of normal display and display of color different from intended color and, in this manufacturing line, a display panel containing, for example, a certain proportion of defective pixels is handled as a defective product.

For example, with respect to the above-mentioned dot omission troubles, in many cases, of hundreds of thousands of or several million pixels constituting a display panel, a very small number of pixels sprinkle as defective pixels. Such a very small number of defective pixels sprinkling in the display panel are not remarkable in use, and there is a tendency that a display panel having defective pixels smaller than a certain proportion of pixels is not handled as a defective product.

So far, there has been a requirement to detect defective pixels in a display panel for preventing the output of a defective product to the market. As such a method of detecting defective pixels in a display panel, for example, the following Patent Document 1 discloses a method of picking up an image of a display screen of a liquid crystal panel to carry out the difference processing on the pickup image, thereby accurately detecting a luminescent spot defect based on an ultra-low-volume difference in luminance and a sun spot defect.

Patent Document 1: Japanese Patent Laid-Open No. HEI 11-119684

Meanwhile, since the line omission troubles are remarkable and frequently unsightly because defective pixels appear continuously in a display panel, it is preferred to detect the line omission troubles more effectively in comparison with the dot omission troubles. Incidentally, such line omission troubles occur principally because foreign matters get mixed between electrodes of a display panel.

Moreover, the line omission trouble of the display panel also occurs due to, for example, the thermal expansion of electrodes, insulating materials and foreign matters getting mixed into the display panel stemming from an increase in temperature in the interior of the display panel, short circuits (semi-contact troubles) between electrodes arising in a case in which the display panel vibrates to move foreign matters therein, or disconnection or breaks (semi-disconnection troubles) of electrode lines and, in many cases, for example, the semi-contact troubles or semi-disconnection troubles occur temporarily (in an instant) because of being involved in variations of operating environment on the display panel such as variations in temperature in the interior of the display panel and vibrations of the display panel itself.

There is a problem which arises with the conventional technique, however, in that difficulty is experienced in detecting the line omission troubles occurring temporarily. For example, the technique of the above-mentioned Patent Document 1 is made to only once pick up an image of the display screen and, hence, the non-occurrence of a semi-contact trouble or semi-disconnection trouble at the image pickup makes it difficult to detect these troubles, which can cause a line omission trouble to occur during use afterwards even in a case in which no line omission trouble is detected by the inspection conducted when the display panel is put on the market from the factory.

In addition, in the case of the technique disclosed in the above-mentioned Patent Document 1, if the image pickup of the display screen is made more than once, the inspection time to be taken for each display panel lengthens, which leads to incurring an increase in operator's burden or manufacturing cost.

SUMMARY OF THE INVENTION

The present invention has been developed in consideration of the above-mentioned problems, and it is therefore an object of the invention to reliably and easily carry out a detection of defective pixels temporarily occurring due to, for example, variations of operating environments such as semi-contact troubles or semi-disconnection troubles.

For the above-mentioned purpose, in accordance with the present invention, there is provided a display panel inspection apparatus made to inspect a display panel composed of a plurality of pixels, comprising a detecting unit detecting whether or not each of the pixels is a defective pixel and a holding unit holding a result of the detection by the detecting unit.

Preferably, the detecting unit includes an optical detecting unit generating a detection state corresponding to output light from the pixel and a judging unit, on the basis of the detection state, making a judgment as to whether or not the pixel is a defective pixel and outputting a detection signal when the judgment shows that the pixel is a defective pixel, and the holding unit holds a state of the detection signal outputted from the judging unit.

In addition, preferably, the optical detecting unit includes a plurality of optical detection elements disposed according to an arrangement direction of the plurality of pixels and the judging unit includes a plurality of defective pixel deciding units respectively connected in a state associated with the plurality of optical detecting elements and the holding unit includes a plurality of latch units respectively connected in a state associated with the plurality of optical detecting elements.

Still additionally, it is also appropriate that the plurality of optical detecting elements are disposed along one side of the display panel having a rectangular configuration, or that the plurality of optical detecting elements are disposed along a diagonal line of the display panel having a rectangular configuration.

Yet additionally, the display panel inspection apparatus further comprises a notifying unit notifying the output of the detection signal from the judging unit.

Moreover, preferably, the display panel inspection apparatus further comprises an operating environment changing unit changing an operating environment on the display panel.

Still moreover, preferably, the operating environment changing unit includes a temperature environment changing unit changing a temperature environment on the display panel.

Yet moreover, it is also appropriate that the operating environment changing unit includes a vibration applying unit applying vibration to the display panel.

Furthermore, in accordance with the present invention, there is provided a display panel inspection method of inspecting a display panel composed of a plurality of pixels, comprising a detection step of detecting whether or not each of the pixels is a defective pixel and a hold step of holding a result of the detection in the detection step.

Preferably, the detection step comprises an optical detection step of generating a detection state corresponding to output light from the pixel and a judgment step of, on the basis of the detection state, making a judgment as to whether or not the pixel is a defective pixel and of outputting a detection signal when the judgment shows that the pixel is a defective pixel, with a state of the detection signal outputted in the judgment step being held in the hold step.

In addition, preferably, the optical detection step is conducted more than once according to an arrangement direction of the plurality of pixels and the judgment step and the hold step are conducted in a state associated with each of the optical detection steps conducted more than once.

Still additionally, it is also appropriate that the optical detection step is conducted along one side of the display panel having a rectangular configuration, or that the optical detection step is conducted along a diagonal line of the display panel having a rectangular configuration.

Yet additionally, the display panel inspection method further comprises a notification step of notifying that the detection signal is outputted in the judgment step.

Moreover, preferably, the display panel inspection method further comprises an operating environment changing step of changing an operating environment on the display panel.

Still moreover, preferably, a temperature environment on the display panel is changed in the operating environment changing step.

Yet moreover, it is also appropriate that vibration is applied to the display panel in the operating environment changing step.

The present invention is designed to detect that a pixel is a defective pixel and to hold a result of the detection, which enables a detection of a line omission trouble to be made reliably even in a case in which a line omission trouble stemming from a semi-contact trouble, semi-disconnection trouble or the like occurs temporarily. In addition, the result of the detection of the temporally occurred line omission trouble can be confirmed after the completion of the inspection, which eliminates the need for an inspector to make the confirmation through visual observation during the inspection, thereby reducing the working burden on the inspector. This can improve the detection accuracy of the line omission trouble without imposing a burden on the inspector.

Moreover, a judgment as to whether a pixel is a defective pixel is made on the basis of the detection state corresponding to the output light of the pixel, thereby reliably and easily specifying the spot where the line omission trouble has occurred.

Still moreover, since the operating environment on the display panel is changeable, it is possible to reliably detect the line omission troubles occurring with various variations of the operating environment.

In particular, the change of the temperature environment related to the display panel can achieve the reliable detection of a line omission trouble occurring due to the thermal expansion of electrodes, insulating materials and foreign matters stemming from an increase in temperature in the interior of the display panel.

Furthermore, the arrangement of the plurality of optical detecting units along one side of the display panel enables the detection of the line omission trouble to be made within a short period of time. Still furthermore, the numbers of optical detecting units, judging units and holding units are reducible, which can simplify the apparatus configuration and decrease the manufacturing cost.

The notification on the output of a detection signal by the judging unit allows easily specifying the spot where a line omission trouble has occurred.

DESCRIPTION OF THE PREFERRED EMBODIMENTS

Embodiments of the present invention will be described hereinbelow with reference to the drawings.

[1] Description of Embodiment of the Present Invention

Figure 1:
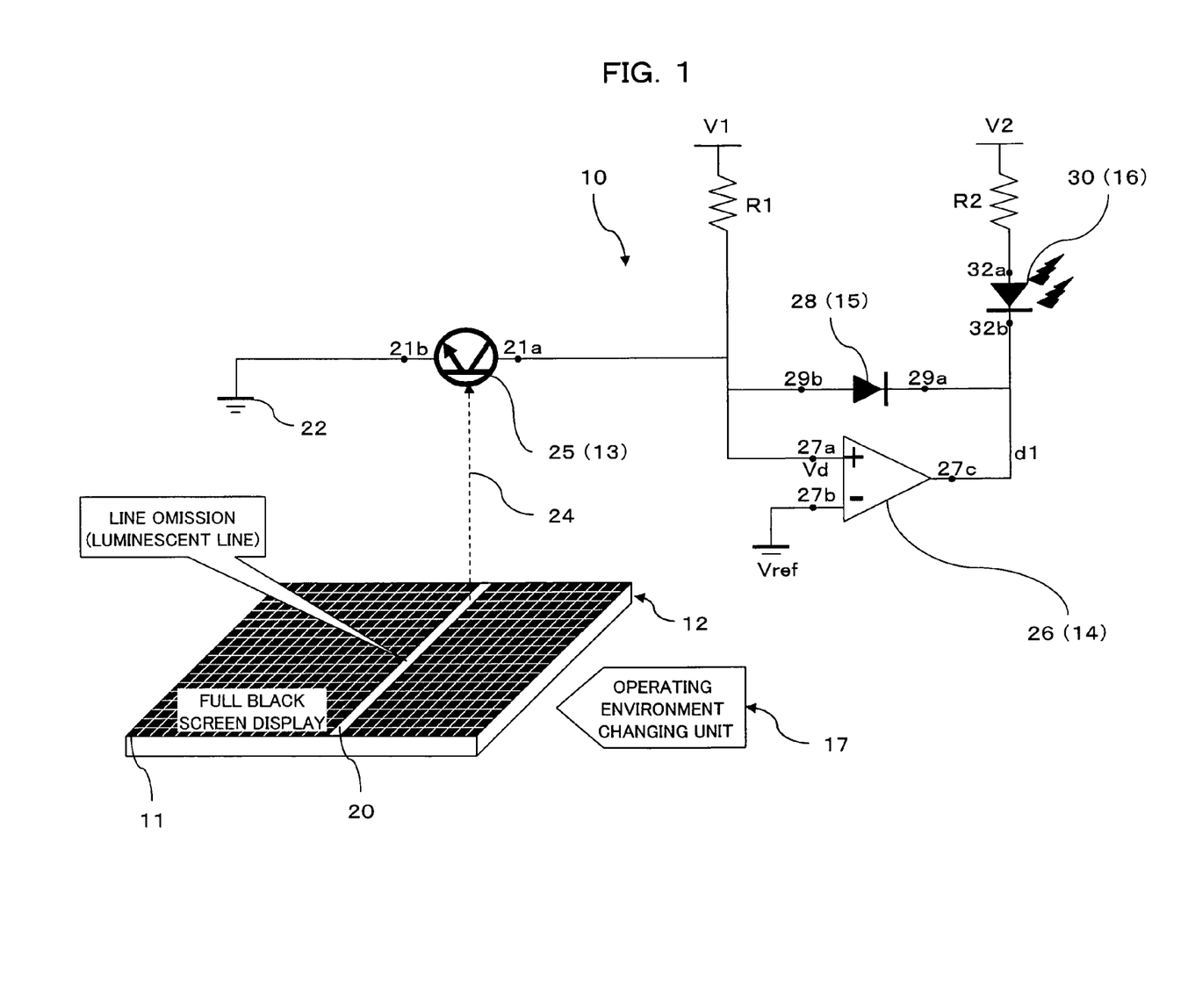
FIG. 1 illustratively shows an example of a configuration of a display panel inspection apparatus according to an embodiment of the present invention.
Figure 2:
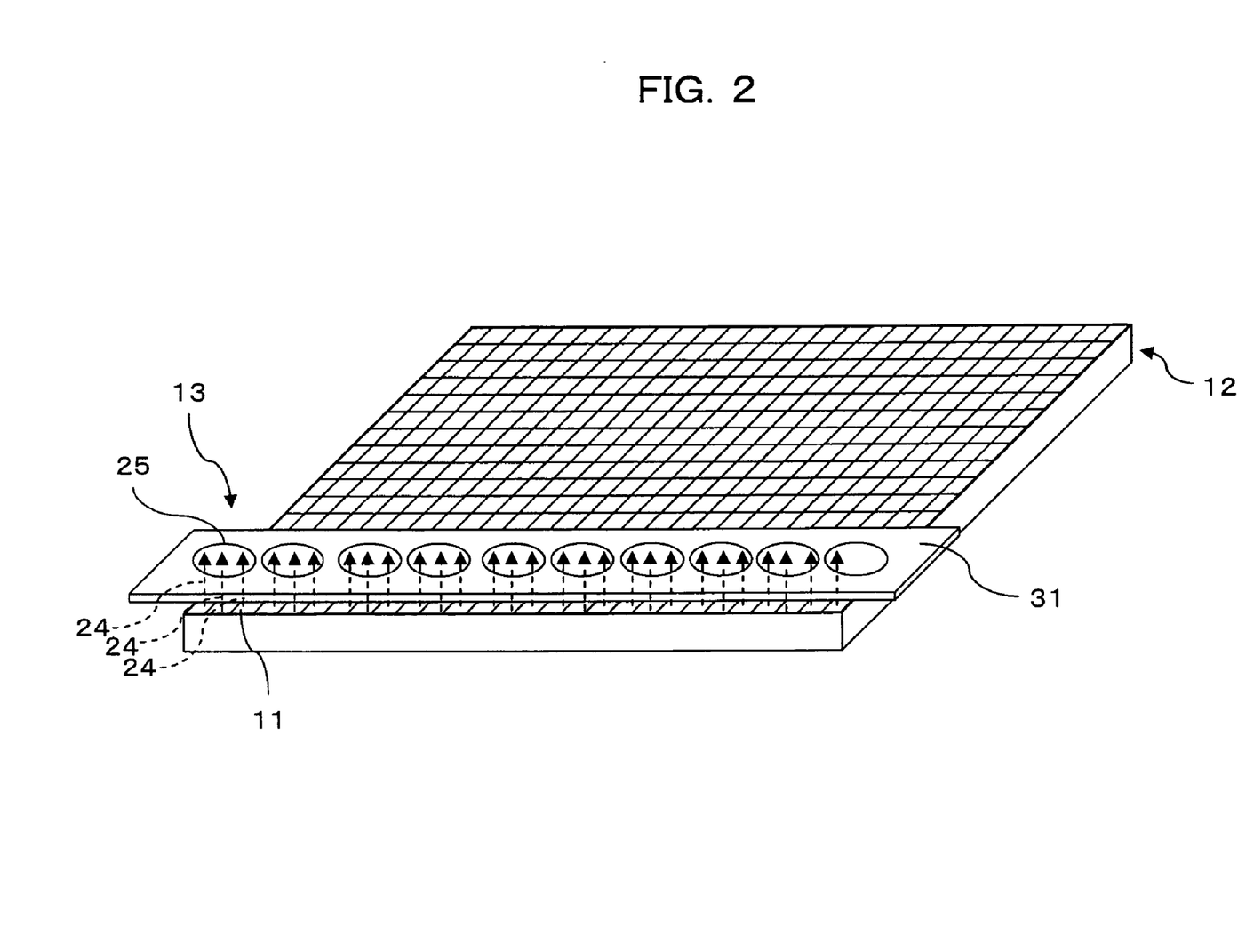
FIG. 2 is an illustration useful for explaining an example of a disposition state in an optical detecting unit of a display panel inspection apparatus according to an embodiment of the present invention.
Figure 3:
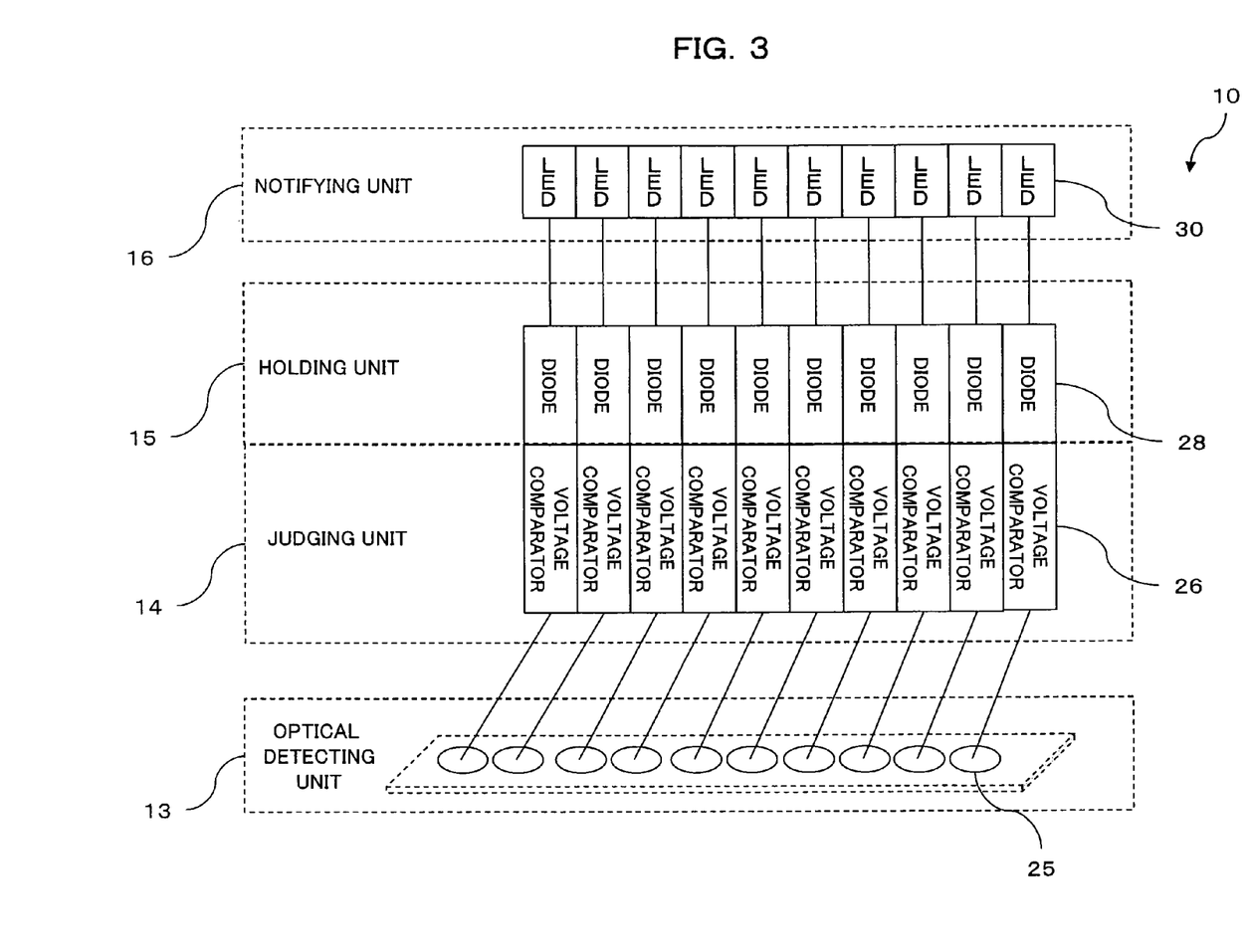
FIG. 3 is an illustration useful for explaining a connection state from an optical detecting unit to a notifying unit in a display panel inspection apparatus according to an embodiment of the present invention.

FIG. 1 illustratively shows an example of a configuration in a case in which a luminescent line is detected as a line omission trouble in a display panel inspection apparatus according to an embodiment of the present invention, FIG. 2 is an illustration useful for explaining an example of a disposition state in an optical detecting unit thereof, and FIG. 3 is an illustration useful for explaining a connection state from an optical detecting unit to a notifying unit therein.

As shown in FIG. 1, a display panel inspection apparatus 10 according to this embodiment is an apparatus for inspecting a line omission trouble in a rectangular LCD (Liquid Crystal Display; display panel) 12 composed of a plurality of pixels 11 and is configured as an electric circuit including an optical detecting element (detecting unit, optical detecting unit) 25, a voltage comparator (judging unit, detecting unit, defective pixel judging unit) 26, a diode (holding unit, latch unit) 28 and an LED (Light Emitting Diode; notifying unit) 30, and further equipped with an operating environment changing unit 17.

The line omission trouble signifies that, of a plurality of pixels constituting an LCD, defective pixels which cannot fulfill their intended functions appear continuously in the form of a line and, in this embodiment, a description will be given of an example of a line omission trouble in which a luminescent line 20 appears in a case in which a color low in luminance, such as block, is displayed throughout a surface of an LCD 12 as shown in FIG. 1.

An LCD commonly put on the market is composed of hundreds of thousands of or several million pixels and, although this embodiment is also configured so as to handle an LCD having hundreds of thousands of or several million pixels, a portion of the pixels is omitted from the illustration for convenience only.

Moreover, in the following description of pixels, a plurality of pixels are referred to as a plurality of pixels 11 and a single pixel is referred to simply as a pixel 11.

In this display panel inspection apparatus 10, an optical detecting element 25 is designed as a photodiode having a collector side terminal 21a and an emitter side terminal 21b, and the voltage comparator 26 and the diode 28 are connected in parallel at the collector side terminal 21a of the optical detecting element 25. In addition, an LED 30 is connected to the output sides of the voltage comparator 26 and the diode 28. A power supply unit (not shown) is connected through a resistor R2 to the LED 30 so as to supply an applied voltage V2 through the resistor R2. A power supply unit (not shown) is connected through a resistor R1 to the collector side terminal 21a of the optical detecting element 25, thereby supplying an applied voltage V1 through the resistor R1. Still additionally, the emitter side terminal 21b of the optical detecting element 25 is connected to a ground 22.

As FIG. 1 shows, each of the optical detecting elements 25 (detecting unit) is for generating a detection state corresponding to an output light of the pixel 11 and functions as an optical detecting unit 13 which will be mentioned later.

In response to the detection of the output light 24, this optical detecting element 25 increases a current quantity therein according to the light quantity of the output light 24 so as to lower a collector side voltage Vd of the optical detecting element 25 from the applied voltage V1, and this voltage drop serves as a detection state.

Incidentally, as the optical detecting element 25, there is used a device made to convert light (or quantity thereof) from the above-mentioned phototransistor, a photodiode, a CCD (Charge Coupled Device) or the like into an electric signal (current, voltage).

The light quantity of the output light 24 to be detected by the optical detecting element 25 can be arbitrarily set according to a criterion of judgment for a line omission trouble or a circuit arrangement and, for example, various setting can be made by adjusting the S/N ratio in the interior of the optical detecting element 25 or by changing/adjusting the resistors R1, R2 or the value of a reference voltage Vref which will be mentioned later.

In the display panel inspection apparatus 10 according to this embodiment, as shown in FIG. 2, a plurality of optical detecting elements 25 are disposed along one side of the LCD 12 having a rectangular configuration, and these plurality of optical detecting elements 25 is equally referred to as an optical detecting unit 13 (see FIG. 3).

As FIG. 2 shows, the plurality of optical detecting elements 25 is fixedly secured to a plate 31 in a line along one side of the LCD 12 (in a transverse direction of paper in the example shown in FIG. 2) having a rectangular configuration. In the example shown in FIG. 2, one optical detecting element 25 is principally made to detect the output lights 24 of three pixels 11 adjacent to each other. Moreover, the distance between the LCD 12 and the optical detecting element 25 is determined on the basis of the characteristic of the optical detecting element 25.

The voltage comparator (detecting unit, defective pixel judging unit) 26 is made as shown in FIG. 1 so as to, on the basis of a detection state by the optical detecting element 25, make a judgment as to whether or not the pixel 11 is a defective pixel and, if the judgment shows that the pixel 11 is a defective pixel, output a detection signal d1.

The voltage comparator 26 is designed as an operational amplifier having a + input terminal 27a, a − input terminal 27b and an output terminal 27c. The + input terminal 27a is connected to the collector side terminal 21a of the optical detecting element 25 and the output terminal 27c is connected to an LED 30, with a reference voltage Vref being applied to the − input terminal 27b. This reference voltage Vref can be arbitrarily set at a value lower than the applied voltage V1 according to a criterion of judgment on the line omission trouble.

In a case in which a result of the comparison between a detection voltage Vd of the + input terminal 27a and the reference voltage Vref of the − input terminal 27b in the voltage comparator 26 shows that the detection voltage Vd is higher than the reference voltage Vref, the voltage level of the output terminal 27c becomes a High state. On the other hand, when the detection voltage Vd is lower than the reference voltage Vref, the voltage level of the output terminal 27c becomes a Low state. Thus, the state where the voltage level becomes Low at the output terminal 27c serves as a detection signal d1.

As shown in FIG. 3, this voltage comparator 26 is provided in corresponding relation to each of the optical detecting elements 25, and these plurality of voltage comparators 26 are equally referred to as a judging unit 14.

The diode (holding unit, latch unit) 28 is for holding (latching) the detection signal d1 outputted from the voltage comparator 26 as shown in FIG. 1 and functions as a holding unit 15 which will be mentioned later, and a cathode side terminal 29a thereof is connected to the LED 30 while an anode side terminal 29b thereof is connected to the collector side terminal 21a of the optical detecting element 25.

As shown in FIG. 3, this diode 28 is provided in corresponding relation to each of the optical detecting elements 25, and these plurality of diodes 28 are equally referred to as a holding unit 14.

The LED (notifying unit) 30 is for notifying to the external (for example, inspector) the fact that the detection signal d1 has been outputted from the voltage comparator 26, and lights up in a case in which the detection signal d1 is outputted from the voltage comparator 26, that is, when the voltage level becomes a Low state at the output terminal 27c. Thus, it functions as a notifying unit 16. Moreover, as shown in FIG. 1, in the LED 30, a cathode side terminal 32b thereof is connected to the output side terminal 27c of the voltage comparator 26 while anode side terminal 32a thereof is connected to a resistor R2.

As FIG. 3 shows, this LED 30 is provided in corresponding relation to each of the optical detecting elements 25, and these plurality of LEDs 30 are equally referred to as a notifying unit 16.

The operating environment changing unit 17 is for changing an operating environment for the display panel 12 and, for example, it is equipped with a humidifier/cooler or the like (temperature environment changing unit) for changing a temperature environment related to the LCD 12 by humidifying/cooling the LCD 12 with the optical detecting unit in a circled condition up to an arbitrary temperature or with a vibration applying unit for applying vibration to the LCD 12. These humidifier, cooler and vibration applying unit are realizable with various types of existing techniques.

That is, as shown in FIG. 3, the display panel inspection apparatus 10 according to this embodiment is equipped with the judging unit 14 and the holding unit 15 at the collector side terminals 21a of the optical detecting unit 13. The judging unit 14 is composed of a plurality of voltage comparators (defective pixel judging units) 26 respectively connected to the plurality of optical detecting units 25 in corresponding relation, and the holding unit 15 is composed of a plurality of diodes (latch units) 28 respectively connected to the plurality of optical detecting units 25 in corresponding relation. The notifying unit 16 is provided on the output sides of the judging unit 14 and the holding unit 15, and this notifying unit 16 is composed of a plurality of LEDs 30 respectively connected to the plurality of voltage comparators 26 and the plurality of diodes 28 in corresponding relation.

Figure 4:
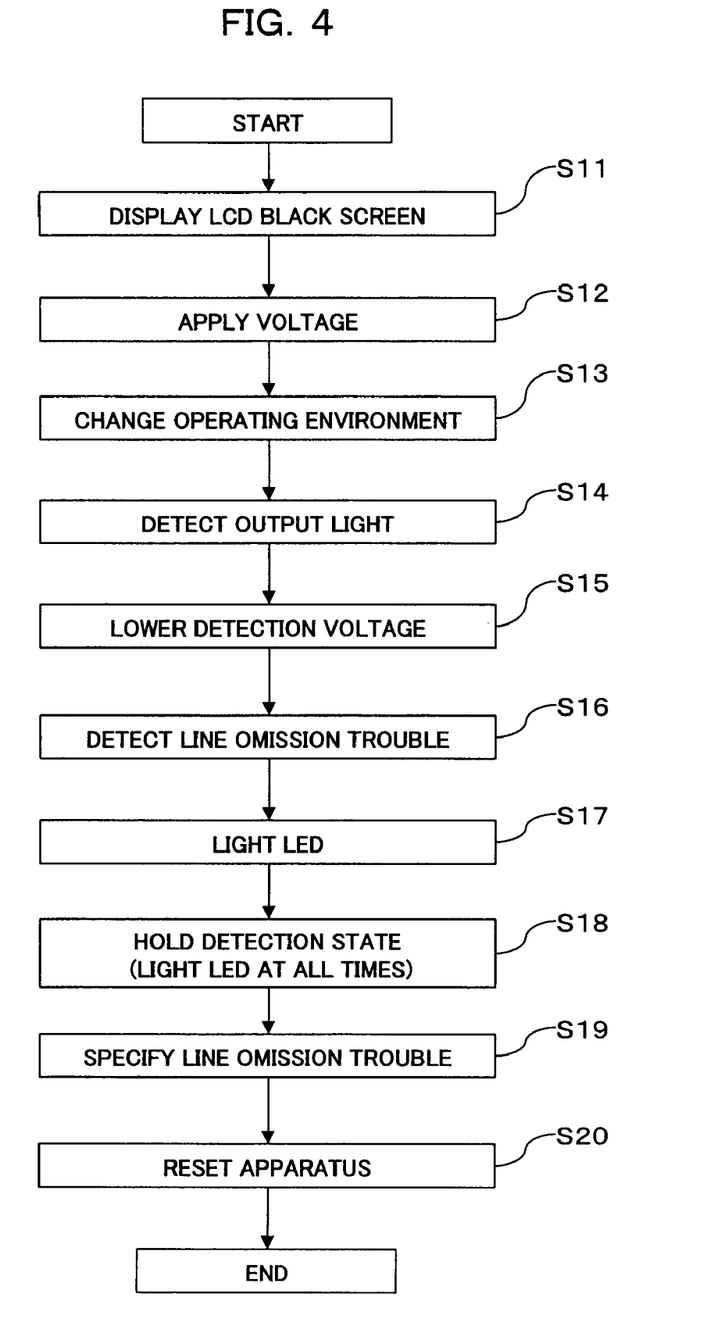
FIG. 4 is a flow chart showing a procedure for detecting a luminescent line as a line omission trouble in a display panel inspection apparatus according to an embodiment of the present invention.

Referring to a flow chart (steps S11 to S20) of FIG. 4, a description will be given hereinbelow of a procedure of detecting a luminescent line 20 as a line omission trouble by the display panel inspection apparatus 10 thus configured according to this embodiment.

First of all, an inspector positions the light receiving portions (not shown) of the optical detecting elements 25 (optical detecting unit 13) above the light emitting surfaces of the pixels 11 which are an object of inspection so that they confront each other, and places all the plurality of pixels 11 constituting the LCD 12 into a black screen displaying state (step S11).

Following this, an applied voltage V1 is applied to the resistor R1 and an applied voltage V2 is applied to the resistor R2. Moreover, a reference voltage Vref lower than the applied voltage V1 is applied to the − input terminals 27b of the voltage comparators 26 so that the voltage level of the output terminals 27c are placed into a High state (step S12). Still moreover, through the use of the operating environment changing unit 17, the temperature environment on the LCD 12 is changed or the LCD 12 is vibrated (step S13; operating environment changing step).

In this state, if a line omission trouble (luminescent line 20) occurs among the pixels 11 which are an object of inspection, the pixels 11 causing the line omission trouble output the output lights 24 (emit lights), and the optical detecting elements 25 disposed to confront the pixels 11 outputting the output lights 24 detect the output lights from the luminescent line 20 (step S14).

In response to the detection of the output lights 24 from the luminescent line 20, the optical detecting elements 25 increase the current quantities of the optical detecting elements 25 according to the light quantities of the output lights 24, so the detection voltages Vd of the + input terminals 27a of the voltage comparators 26 drop with respect to the applied voltage V1 (step S15; optical detection step, detection step).

Each of the voltage comparators 26 sets the voltage level of the output terminal 27c from a High state to a Low state in a case in which the result of the comparison between the detection voltage Vd of the + input terminal 27a and the reference voltage Vref of the − input terminal 27b shows that the detection voltage Vd becomes lower than the reference voltage Vref. This generates an electric potential difference between the output terminal 27c and the resistors R1 and R2 (step S16; judgment step, detection step).

Thus, a current flows from the resistor R1 through the diode 28 to the output terminal 27c of the voltage comparator 26 and a current flow from the resistor R2 through the LED 30 to the output terminal 27c of the voltage comparator 26, so the LED 30 lights up (step S17; notification step)

Moreover, even in a case in which the output light 24 appears from the LCD 12 in an instant, the voltage level of the output terminal 27c is maintained in a Low state, and the diode 28 continues the flow of a current from the resistor R1 through the diode 28 to the output terminal 27c of the voltage comparator 26, thereby maintaining the detection voltage Vd in a state lower than the reference voltage Vref (step S18; hold step)

Therefore, the voltage level of the output terminal 27c of the voltage comparator 26 is maintained in the Low state by the diode 28 and a current from the resistor R2 continuously flows through the LED 30 to the output terminal 27c of the voltage comparator 26, so the LED 30 lights at all times.

The inspector can seize the occurrence of a line omission trouble by confirming the lighting state of the LED 30 through visual observation and, on the basis of the location of the optical detecting element 25 corresponding to this lighting LED 30, specifies the spot where the luminescent line 20 has appeared as a line omission trouble (step S19). Thereafter, the inspector lowers the reference voltage Vref of the circuit, where the LED 30 lights, up to a value below the detection voltage Vd to put out the LED 30, and resets the display panel inspection apparatus 10 (step S20). Thus, the inspection comes to an end.

Since as described above the display panel inspection apparatus 10 according to embodiment of the present invention is designed to detect the pixels 11 where a line omission trouble has occurred as the luminescent line 20 and hold the detection result, even in a case in which the temporary output lights 24 are emitted due to the line omission trouble such as a semi-contact trouble or semi-disconnection trouble, it is possible to recognize the occurrence of the line omission trouble and further to reliably specify the pixels 11 where the line omission trouble has occurred. In addition, since a result of the detection on the output lights 24 stemming from the line omission trouble which has occurred temporarily can be confirmed after the completion of the inspection, there is no need for the inspector to make the confirmation through visual observation during the inspection, which can reduce the working burden on the inspector. Therefore, it is possible to improve the accuracy on the detection of a line omission trouble without imposing a burden on the inspector.

Moreover, since a judgment as to whether or not the pixel 11 is a defective pixel is made on the basis of a detection state of the output light 24 from the pixel 11, only by detecting the output light 24 from the pixel 11, it is possible to reliably and easily specify the pixel 11 where a line omission trouble has occurred.

Still moreover, since the operating environment for the LCD 12 can be changed by varying the temperature applied to the LCD 12 or by vibrating the LCD 12, the detection of a possible line omission trouble can be made under various operating environments.

Yet moreover, the arrangement of a plurality of optical detecting elements 25 along one side of the LCD 12 enables a line omission trouble to be detected within a short period of time. Add to it that the numbers of optical detecting elements 25, voltage comparators 26, diodes 28 and LEDs 30 are reducible, thereby simplifying the apparatus configuration and reducing the manufacturing cost.

Furthermore, it is possible to visually specify the spot where a line omission trouble has occurred, by notifying a result of the detection on the output light 24 through the use of the LED 30.

[2] Others

It should be understood that the present invention is not limited to the above-described embodiment, and that it is intended to cover all changes and modifications of the embodiment of the invention herein which do not constitute departures from the spirit and scope of the invention.

For example, although in the above-described embodiment a line omission trouble is detected as a luminescent line 20 throughout a full block screen display, the present invention is not limited to this, but it is also appropriate that a dark line is detected as a line omission trouble in a case in which a screen high in luminance, such as white, is displayed throughout a surface of an LCD (which will be referred to hereinafter as a full white screen display).

Figure 5:
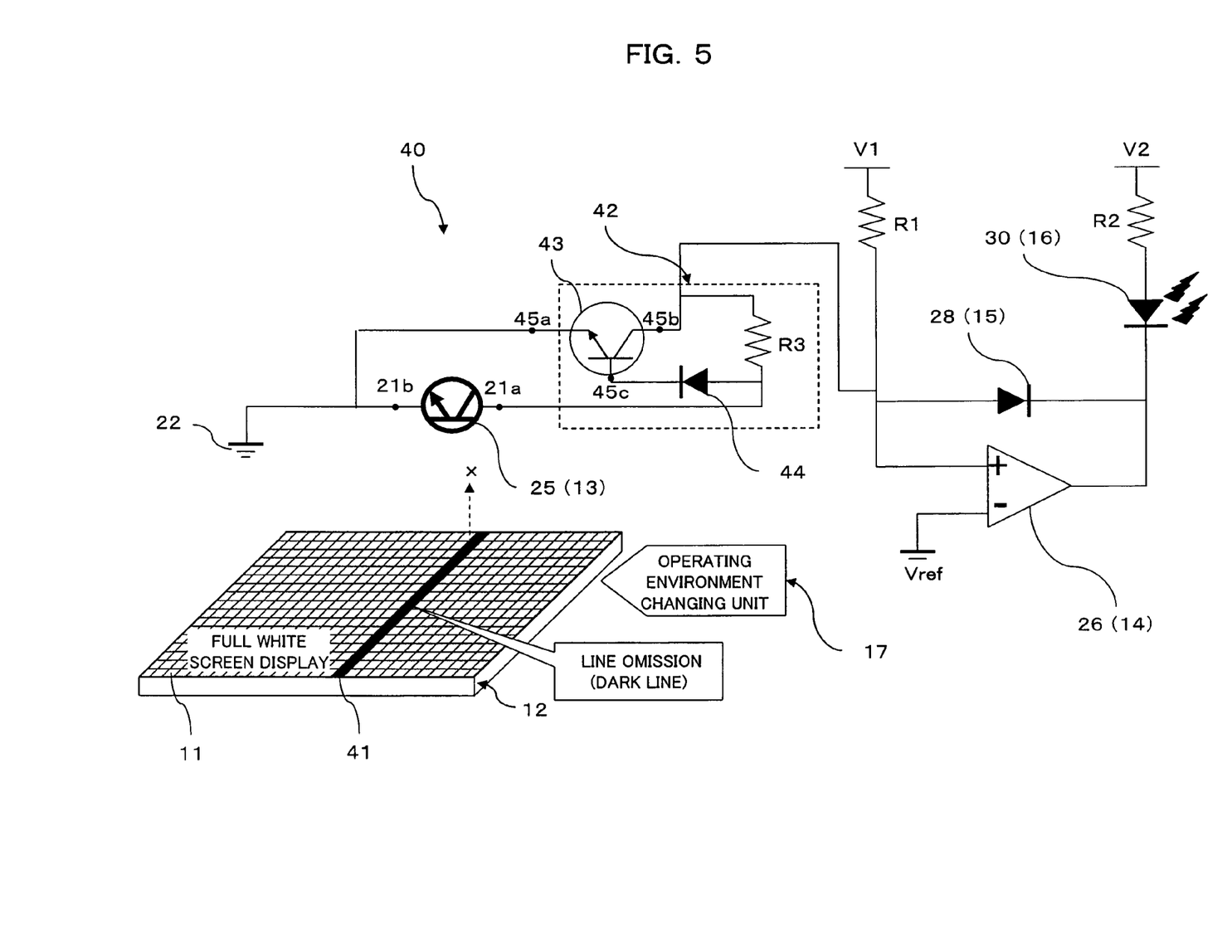
FIG. 5 illustratively shows an example of a configuration of a display panel inspection apparatus according to a first modification of an embodiment of the present invention.

FIG. 5 is an illustration of a display panel inspection apparatus according to a first modification of the embodiment of the present invention, and illustratively shows an example of a configuration of a display panel inspection apparatus 40 in a case in which a dark line 41 is detected as a line omission trouble.

In the illustration, the same reference numerals as those used above designate the same or generally same parts, and the detailed description thereof will be omitted for brevity.

The display panel inspection apparatus 40 shown in FIG. 5 is provided with, in addition to the components of the display panel inspection apparatus 10 shown in FIG. 1, a signal inverting circuit 42 positioned between the optical detecting element (optical detecting unit) 25 and the upstream side of the resistor R1. This signal inverting circuit 42 is made to invert (reverse) a detection state from the optical detecting element 25, with the inverted detection state being outputted to the voltage comparator (judging unit) 26 and the diode (holding unit) 28.

For example, as shown in FIG. 5, the signal inverting circuit 42 is composed of a resistor R3, a transistor 43 and a diode 44. The resistor R3 is connected to the resistor R1 at its one end portion and further connected to the collector side terminal 21a of the optical detecting element 25 at its other end portion. The transistor 43 is of an NPN type having an emitter side terminal 45a, a collector side terminal 45b and a base side terminal 45c, and the emitter side terminal 45a is connected to the emitter side terminal 21b of the optical detecting element 25 while the collector side terminal 45b is connected to one end sides of the resistor R1 and the resistor R3. Moreover, the base side terminal 45c is connected to a cathode side terminal (whose reference numeral is omitted) of the diode 44. In the diode 44, its cathode side terminal (whose reference numeral is omitted) is connected to the base side terminal 45c of the transistor 43 and its anode side terminal (whose reference numeral is omitted) is connected to the collector side terminal 21a of the optical detecting element 25 and the other end side of the resistor R3.

Incidentally, an arrangement other than the above-described arrangement is also employable as the signal inverting circuit 42, and it is also possible to use various types of existing techniques of inverting the detection state generated by the optical detecting unit 13 and inputting the inverted detection state to the voltage comparator 26 (judging unit 14) and the diode 28 (holding unit 15).

In this display panel inspection apparatus 40, when the optical detecting unit 13 does not detect the output lights from the pixels 11 (dark line 41), the current quantity of the optical detecting element 25 is increased so as to lower the collector side voltage of the optical detecting element 25 with respect to the applied voltage V1 so that the voltage comparator makes a decision that the formed portion of a luminescent line is normal and that the formed portion of the dark line 41 creates a line omission trouble.

In addition, it is also appropriate to detect both the above-mentioned luminescent line 20 and dark line 41.

Figure 6:
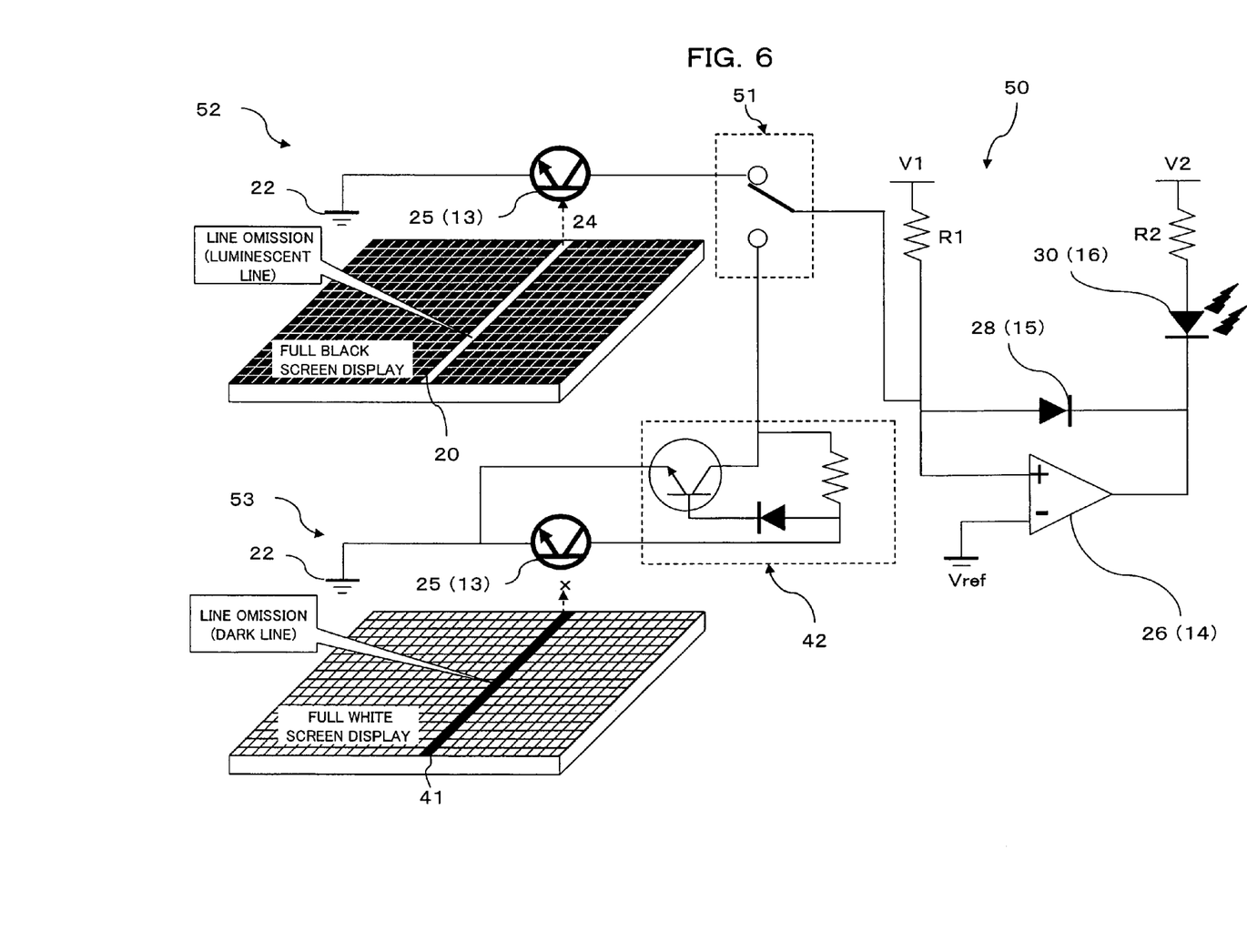
FIG. 6 illustratively shows an example of a configuration of a display panel inspection apparatus according to a second modification of an embodiment of the present invention.

FIG. 6 illustratively shows an example of a configuration of a display panel inspection apparatus according to a second modification of the embodiment of the present invention, and shows a configuration of a display panel inspection apparatus 50 which can detect both a luminescent line and a dark line in a switching fashion.

In the illustration, the same reference numerals as those used above designate the same or generally same parts, and the detailed description thereof will be omitted for brevity.

The display panel inspection apparatus 50 shown in FIG. 6 comprises a luminescent line detection circuit 52 equipped with an optical detecting unit 13 and a dark line detection circuit 53 equipped with an optical detecting unit 13 and a signal inverting circuit 42, and further comprises a change-over switch 51 provided between the optical detecting unit 13 of the luminescent detection circuit 52 and a voltage comparator 26, a diode 28 for carrying out the switching between the luminescent line detection circuit 52 and the dark line detection circuit 53 for the connection to the diode 28 and the voltage comparator 26.

In the display panel inspection apparatus 50, the diode 28, the voltage comparator 26, the LED 30 and others can be used in a shared fashion by switching-controlling the change-over switch 51 according to a line omission trouble detected, thereby enhancing the convenience, reducing the manufacturing cost and realizing the saving of space.

Although in this embodiment the output lights 24 of three pixels 11 are detected by one optical detecting element 25, the present invention is not limited to this, but it is also appropriate to increase the number of output lights 24 to be detected by one optical detecting element 25. In this case, the number of output lights 24 to be detected is diversely determined according to the size (area) of a light receiving surface of the optical detecting element 25 or the size of a light remitting surface of the pixel 11 and, in particular, when the optical detecting element 25 is disposed in corresponding relation to each of the pixels 11 so as to detect one output light 24 by one optical detecting element 25, it is possible to easily specify a spot where a line omission trouble has occurred.

Furthermore, it is also appropriate that the optical detecting elements 25 are disposed in a plurality of lines, instead of in one line, on the LCD 12 to specify the spot, where a line omission trouble has occurred, on the basis of the light reception results in the plurality of lines. For example, a plurality of optical detecting elements 25 can be disposed in three lines in a staggered fashion, or the number of lines thereof can be increased to take a different disposition pattern, so that the occurrence place of a line omission trouble is specified on the basis of a combination of the results of the detection by the plurality of optical detecting elements 25.

Still furthermore, although in this embodiment the plurality of optical detecting elements 25 are disposed along one side of the LCD 12 as shown in FIG. 2, the present invention is not limited to this.

Figure 7:
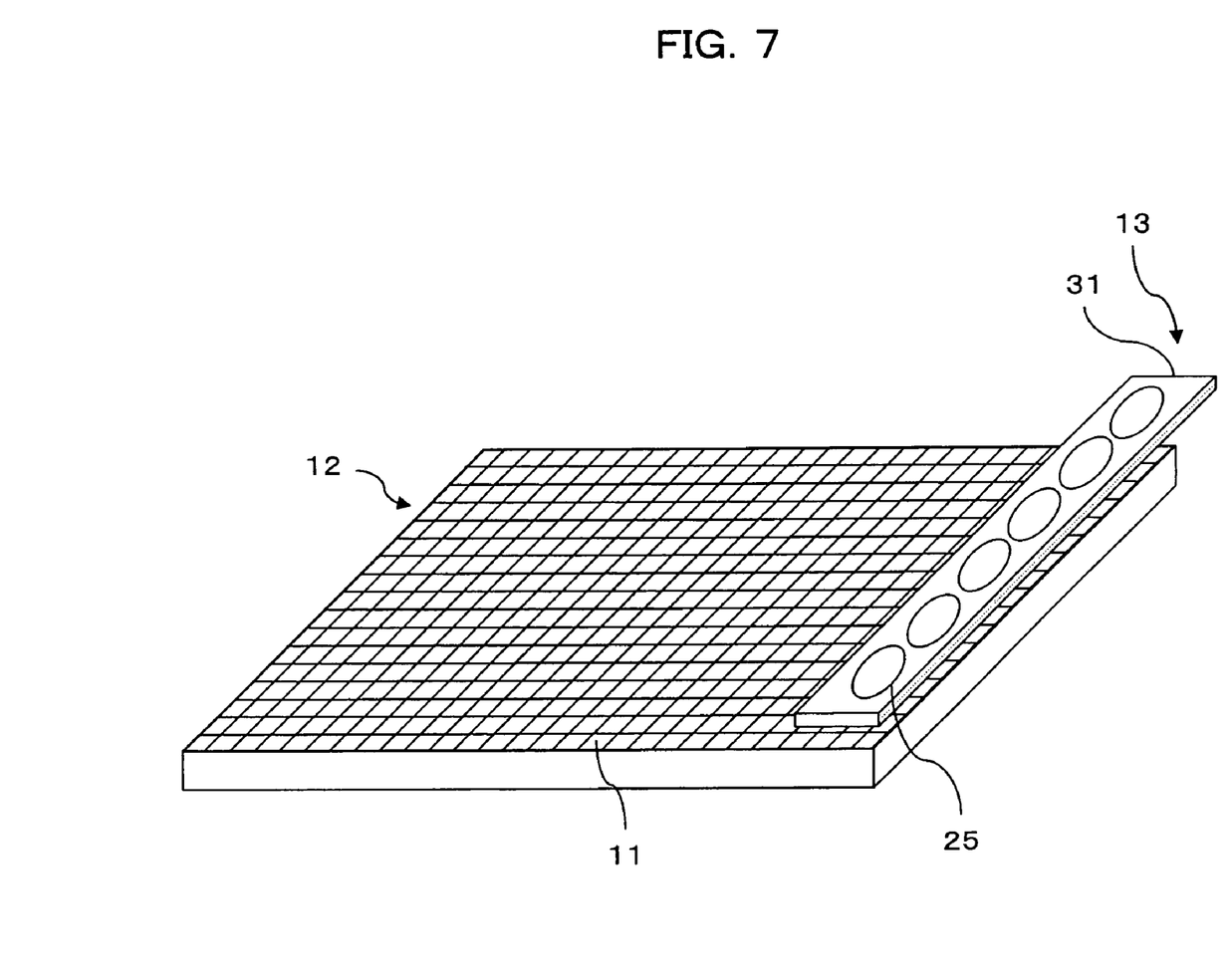
FIG. 7 is an illustration useful for explaining an example of another disposition state in an optical detecting unit of a display panel inspection apparatus according to an embodiment of the present invention.
Figure 8:
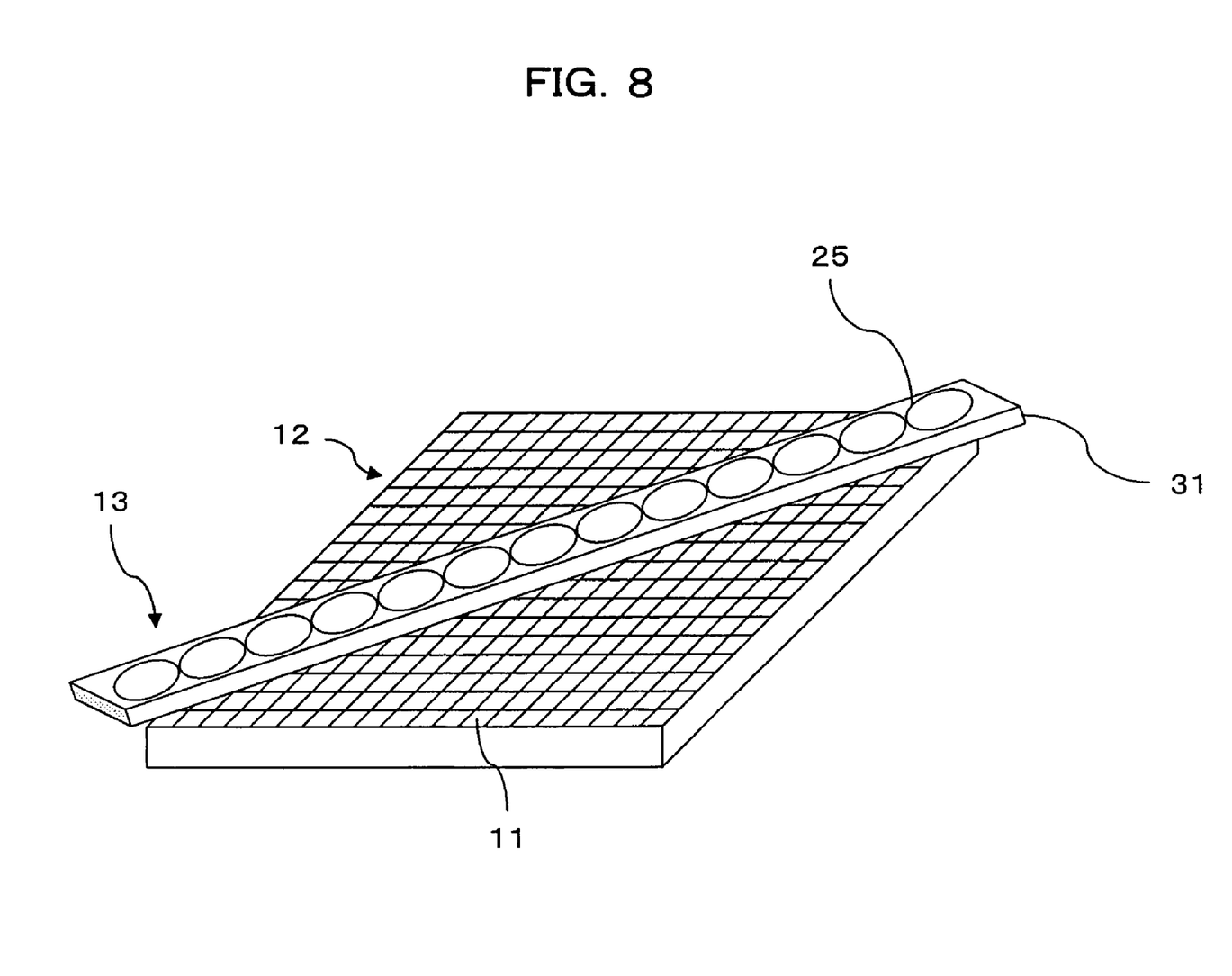
FIG. 8 is an illustration useful for explaining an example of a different disposition state in an optical detecting unit of a display panel inspection apparatus according to an embodiment of the present invention.

FIGS. 7 and 8 are illustrations for explaining different disposition states of optical detecting units in a display panel inspection apparatus according to an embodiment of the present invention. FIG. 7 is an illustration for explaining a disposition state of an optical detecting unit along a different side of an LCD, and FIG. 8 is an illustration for explaining a disposition state of an optical detecting unit along a diagonal line of an LCD.

For example, it is also appropriate that a plurality of optical detecting elements 25 are arranged along a different side of the LCD 12 as shown in FIG. 7 (vertical direction on the paper in the example shown in FIG. 7), or that a plurality of optical detecting elements 25 are arranged along a diagonal line of the LCD 25 as shown in FIG. 8.

When the plurality of optical detecting elements 25 are arranged along a diagonal line of the LCD 12, it is possible to simultaneously detect the output lights 24 from the pixels 11 formed linearly in vertical and horizontal directions of the LCD 12, which enables reduction of the number of optical detecting elements 25 and prompt and reliable detection of a line omission trouble.

In addition, although in this embodiment the voltage comparators 26 are used as the judging unit 14, the present invention is not limited to this, but it is also acceptable to employ various types of existing techniques of, on the basis of a detection state from the optical detecting unit 13, making a judgment as to whether or not the pixel 11 is a defective pixel so that a detection signal d1 is outputted when the judgment shows that it is a defective pixel.

Still additionally, although in this embodiment the diode 28 is used as the holding unit 15, the present invention is not limited to this, but it is also possible to employ various types of existing techniques of holding a detection signal d1 outputted from the judging unit 14. For example, it is also possible to use a circuit having a latch function, such as a flip-flop, in place of the diode 28. Yet additionally, for example, when a flip-flop is used as the holding unit 15, it is preferred that the holding unit 15 is connected in series to the output side of the judging unit 14. That is, this enables the circuit arrangement of the display panel inspection apparatus 10 to be diversely modified according to parts used for the holding unit 15 and others.

Moreover, although in this embodiment the LED 30 is used as the notifying unit 16, the present invention is not limited to this, but it is also acceptable to employ various types of existing techniques of making a notification to the external.

Still moreover, the techniques other than the above-described techniques are also acceptable, and it is also possible to employ various types of existing techniques of detecting that the pixel 11 is a defective pixel and holding the detected state.

Yet moreover, it is also appropriate that the collector side terminals 21a of a plurality of optical detecting elements 25 are connected to a microcomputer (not shown) so as to relatively make a comparison between the voltages of the plurality of optical detecting elements 25. For example, the microcomputer calculates an average value of the voltages of the plurality of optical detecting elements 25 to detect, as the occurrence place of a line omission trouble, a portion having a voltage lower than the average value.

Although in this embodiment the operating environment changing unit 17 is designed to include a humidifier, a cooler and a vibration applying unit, the present invention is not limited to this. For example, the operating environment changing unit 17 can be arranged using only a portion of these devices, and it is also acceptable to change the temperature environment such as temperature or change the operating environment other than vibration. It is possible to employ various types of existing techniques for changing these operating environments.

In addition, the above-described display panel inspection apparatus is also applicable to different types of display panels other than LCD and, in particular, it is effective to a dot matrix type display panel, for example, is applicable to a PDP (Plasma Display Panel) or organic EL display (Organic Electroluminescence Display).

What is claimed is:

1. A display panel inspection apparatus, which inspects a display panel composed of a plurality of pixels, comprising:
   a detecting unit detecting whether or not each of said pixels is a defective pixel; and
   a holding unit holding a result of the detection by said detecting unit,
   wherein
      said detecting unit includes an optical detecting unit generating a detection state corresponding to output light from said pixel and a judging unit, on the basis of the detection state, making a judgment as to whether or not said pixel is a defective pixel and outputting a detection signal when the judgment shows that said pixel is a defective pixel,
      said holding unit holds a state of the detection signal outputted from the judging unit,
      said optical detecting unit includes a plurality of optical detection elements disposed according to an arrangement direction of said plurality of pixels,
      said judging unit includes a plurality of defective pixel judging units each connected in corresponding relation to each of said plurality of optical detecting elements, and
      said holding unit includes a plurality of latch units each connected in corresponding relation to each of said plurality of optical detecting elements.

2. The display panel inspection apparatus according to claim 1, wherein said plurality of optical detecting elements are disposed along one side of said display panel having a rectangular configuration.

3. The display panel inspection apparatus according to claim 1, wherein said plurality of optical detecting elements are disposed along a diagonal line of said display panel having a rectangular configuration.

4. The display panel inspection apparatus according to claim 1, further comprising a notifying unit notifying the output of the detection signal from said judging unit.

5. The display panel inspection apparatus according to claim 1, further comprising an operating environment changing unit changing an operating environment on said display panel.

6. The display panel inspection apparatus according to claim 1, further comprising an operating environment changing unit changing an operating environment on said display panel.

7. The display panel inspection apparatus according to claim 5, wherein said operating environment changing unit includes a temperature environment changing unit changing a temperature environment on said display panel.

8. The display panel inspection apparatus according to claim 5, wherein said operating environment changing unit includes a vibration applying unit applying vibration to said display panel.

9. A display panel inspection method of inspecting a display panel composed of a plurality of pixels, comprising:
   (a) detecting whether or not each of said pixels is a defective pixel by:
      (a-1) at a plurality of optical detection elements disposed according to an arrangement direction of said plurality of pixels,
         generating a detection state corresponding to output light from said pixel and (a-2) at a plurality of defective pixel judging units each connected in corresponding relation to each of said plurality of optical detection elements, making a judgment as to whether or not said pixel is a defective pixel on the basis of the detection state and of outputting a detection signal when the judgment shows that said pixel is a defective pixel; and (b) at a holding unit includes a plurality of latch units each connected in corresponding relation to each of said plurality of optical detecting elements.

holding a state of the detection signal outputted in said step (a-2).

10. The display panel inspection method according to claim 9, wherein said optical detection step is conducted more than once according to an arrangement direction of said plurality of pixels, and said judgment step and said hold step are conducted in a state associated with each of said optical detection steps conducted more than once.

11. The display panel inspection method according to claim 10, wherein said optical detection step is conducted along one side of said display panel having a rectangular configuration.

12. The display panel inspection method according to claim 10, wherein said optical detection step is conducted along a diagonal line of said display panel having a rectangular configuration.

13. The display panel inspection method according to claim 9, further comprising a notification step of notifying that the detection signal is outputted in said judgment step.

14. The display panel inspection method according to claim 9, further comprising an operating environment changing step of changing an operation environment on said display panel.

15. The display panel inspection method according to claim 14, wherein a temperature environment on said display panel is changed in said operating environment changing step.

16. The display panel inspection method according to claim 14, wherein vibration is applied to said display panel in said operating environment changing step.

17. The display panel inspection method according to claim 9, further comprising an operating environment changing step of changing an operating environment on said display panel.

* * * * *